(12) United States Patent
Streiff

(10) Patent No.: US 6,394,644 B1
(45) Date of Patent: May 28, 2002

(54) STACKED STATIC MIXING ELEMENTS

(75) Inventor: Felix A. Streiff, Humlikon (CH)

(73) Assignee: Koch-Glitsch, Inc., Wichita, KS (US)

( * ) Notice: Subject to any disclaimer, the term of this patent is extended or adjusted under 35 U.S.C. 154(b) by 0 days.

(21) Appl. No.: 09/596,499

(22) Filed: Jun. 19, 2000

Related U.S. Application Data

(60) Provisional application No. 60/140,336, filed on Jun. 21, 1999.

(51) Int. Cl.[7] .................................. B01F 5/06
(52) U.S. Cl. ...................................... 366/337
(58) Field of Search .......................... 366/181.5, 336, 366/337, 340; 261/112.2; 138/37–40, 42; 48/189.4

(56) References Cited

U.S. PATENT DOCUMENTS

| 1,778,790 | A | * | 10/1930 | Brandl et al. | |
|---|---|---|---|---|---|
| 2,567,998 | A | * | 9/1951 | Griffith | |
| 2,669,946 | A | * | 2/1954 | Peyton | |
| 3,406,947 | A | * | 10/1968 | Harder | |
| 3,460,580 | A | * | 8/1969 | Carter | |
| 3,923,288 | A | * | 12/1975 | King | |
| 4,208,136 | A | * | 6/1980 | King | |
| 4,220,416 | A | | 9/1980 | Brauner et al. | 366/337 |
| 4,497,751 | A | | 2/1985 | Pluss | |
| 4,497,753 | A | | 2/1985 | Streiff | |
| 4,600,544 | A | * | 7/1986 | Mix | |
| 4,614,440 | A | * | 9/1986 | King | |
| 4,747,697 | A | * | 5/1988 | Kojima | |
| 5,104,233 | A | * | 4/1992 | Kojima | |
| 5,320,428 | A | * | 6/1994 | Streiff | |
| 5,378,063 | A | * | 1/1995 | Tsukada | |
| 5,484,203 | A | * | 1/1996 | King et al. | |
| 5,492,408 | A | * | 2/1996 | Alfare | |
| 5,520,460 | A | * | 5/1996 | Lantz | |
| 5,564,827 | A | * | 10/1996 | Signer | |
| 5,605,399 | A | * | 2/1997 | King | |
| 5,620,252 | A | * | 4/1997 | Maurer | |
| 5,800,059 | A | * | 9/1998 | Cooke et al. | |
| 5,992,465 | A | * | 11/1999 | Jansen | |
| 6,042,263 | A | * | 3/2000 | Mentzer et al. | |
| 6,109,781 | A | * | 8/2000 | Ogasawara et al. | |
| 2001/0053108 | A1 | * | 12/2001 | Jahn et al. | |

FOREIGN PATENT DOCUMENTS

| CH | 678284 | * | 8/1991 |
|---|---|---|---|
| DE | 44 28 813 A | | 2/1996 |
| EP | 63729 | * | 11/1982 |
| EP | 0 070 915 A | | 2/1983 |
| EP | 0 655 275 A | | 5/1995 |
| EP | 0 967 004 A | | 12/1999 |
| WO | 92/14541 | * | 9/1992 |
| WO | 95/09689 | * | 4/1995 |

* cited by examiner

Primary Examiner—Charles E. Cooley
(74) Attorney, Agent, or Firm—Shook, Hardy & Bacon L.L.P.

(57) ABSTRACT

A saddle element for a static mixer includes a generally ring-shaped support structure having a central axis, concentric inner and outer, radially spaced, circumferentially extending surfaces, and first and second axially spaced, generally parallel edge surfaces. The inner surface of the ring-shaped support structure defines a fluid flow path which extends along the central axis. The edge surfaces of the ring-shaped support structure are located in respective generally parallel transverse planes which are essentially perpendicular relative to the central axis. The saddle element also includes a plurality of crossbars that are located in the flow path. The crossbars have a first end which is closer to the transverse plane of the first edge of the ring-shaped support structure than to the transverse plane of the second edge of the ring-shaped support structure. The crossbars also have a second end which is closer to the transverse plane of the second edge of the ring-shaped support structure than to the transverse plane of the first edge of the ring-shaped support structure. The crossbars are arranged in at least two separate intersecting oblique planes, each of which intersecting oblique planes is disposed at an angle relative to the central axis. The saddle elements may be used in a structure which includes four flip-flopped stacked elements.

22 Claims, 3 Drawing Sheets

STACKED STATIC MIXING ELEMENTS

CROSS REFERENCE TO RELATED APPLICATION

Priority benefits under 35 U.S.C.§119(e) are claimed in this application from co-pending provisional application Serial No. 60/140,336, filed on Jun. 21, 1999, the entirety of the disclosure of which is hereby specifically incorporated herein by reference.

BACKGROUND OF THE INVENTION

1. Field of the Invention

The present invention relates to static mixers useful for the continuous mixing of fluids, and particularly for mixing highly viscous fluids such as polymer melts.

2. The State of the Prior Art

Static mixing devices are particularly useful for homogenization of multi-component mixtures and the like. Static mixers also are useful in connection with heat exchangers and/or for plug flow reactors. These devices are simple and easy to use. A particular advantage is that static mixers have no moving parts and as a consequence present no particular sealing and/or maintenance difficulties.

It is known that devices of this type are often used for applications in polymer processing by extrusion or injection molding, involving large pressure drops across the mixer. This generally requires a rugged design involving the use of very thick material and reinforcing components. Smaller size elements may be made by precision casting of stainless steel or stellite. Elements may often be strengthened by welding or brazing individual components into a metal sleeve which then may function as a support for the element.

It is also desired that static mixer devices must generally be accessible for maintenance and cleaning and visual inspection after use. One previously known method to provide access permitting cleaning and inspection is to support individual elements with a satellite type ring as is shown in International Publication WO 95/09689. This construction, however, requires expensive precision casting and costly machined spacer rings. The crossbars must be relatively thick because the weak points are the unsupported, free crossbars.

For heavy duty polymer mixer applications in large pipes (>10") with pressure drops of up to 100 bar, the elements must be welded into individual pipe sections. These sections must then be welded together to present the final mixer. This construction is again very expensive. Furthermore, due to the intricacy of the positioning of the components that are welded together, it is not possible to obtain 100% X-ray inspection of the welds. Accordingly increased wall thickness and hydraulic pressure testing is almost always required.

SUMMARY OF THE INVENTION

The problems and difficulties present in prior art devices are alleviated through the use of the present invention which provides a saddle element design for a static mixer which facilitates the manufacture and construction of the mixer as well as providing an ease of assembly and disassembly to thereby facilitate maintenance and cleaning. In particular, the simple design of the saddle element of the invention enables casting of the element as a monolithic structure whereby welding and brazing and the like are avoided.

In its broadest aspects, the invention provides a saddle element for a static mixer which comprises a generally ring-shaped support structure having a central axis, concentric inner and outer, radially spaced, circumferentially extending surfaces, and first and second axially spaced, generally parallel edge surfaces. The inner surface of the ring-shaped support structure defines a fluid flow path which extends along said axis. The edge surfaces are located in respective generally parallel transverse planes which are essentially perpendicular relative to said axis to facilitate stacking of the elements. The element also includes a plurality of elongated crossbars that are located in the flow path to cause intimate and thorough admixing of the fluids traveling along the flow path. In this regard, the crossbars each have a first end which is closer to the transverse plane of the first edge than to the transverse plane of the second edge and a second end which is closer to the transverse plane of the second edge than to the transverse plane of the first edge. The crossbars are strategically arranged in at least two separate intersecting oblique planes, each of which oblique planes is disposed at an angle relative to said axis.

In a desirable embodiment of the invention, crossbars are arranged in four separate oblique planes, which oblique planes are arranged in two separate pairs of oblique planes. The oblique planes of each pair thereof are disposed in generally parallel, laterally spaced relationship relative to one another. Moreover, the oblique planes of each pair of oblique planes are disposed so as to intersect the oblique planes of the other pair of oblique planes along lines which are generally perpendicular to said axis.

Preferably, at least two of said crossbars are arranged in each of the intersecting oblique planes, and the crossbars of each oblique plane are disposed in generally parallel, laterally spaced relationship.

In one preferred embodiment of the invention, the crossbars of the saddle element are arranged in an elongated, generally w-shaped array having a pair of spaced ends. Such array is disposed so as to extend laterally across the flow path with each end thereof being attached to the inner surface of the ring-shaped support structure. Another preferred aspect of the invention is that two of the oblique planes may be positioned so as to intersect at a line which is disposed essentially in the transverse plane of the first edge and which extends through the axis of the element. Preferably, the first ends of the crossbars of said two of said oblique planes are connected together at said line of intersection.

In a particularly preferred embodiment of the invention, the first end of a selected crossbar of a first oblique plane is attached to the inner surface of the ring-shaped support structure at a location adjacent said first edge, the second end of a selected crossbar of a second oblique plane is attached to the second end of the selected crossbar of the first oblique plane, the first end of a selected crossbar of a third oblique plane is connected to the first end of the selected crossbar of the second oblique plane, the second end of the selected crossbar of the third oblique plane is attached to the second end of a selected crossbar of a fourth oblique plane, and the first end of the selected crossbar of the fourth oblique plane is attached to the inner surface of the ring-shaped support structure at a location adjacent said first edge, said selected crossbars extending across the fluid flow path and presenting the desirable w-shaped array.

Ideally, in accordance with the invention, the intersecting oblique planes intersect at an angle of about 90°. That is to say, the oblique planes are disposed at an angle of about 45° relative to the axis of the ring-shaped support structure. In further accordance with the principles and concepts of the invention, about 4 to 8 crossbars are arranged in each of said oblique planes.

The invention also provides a stacked static mixer structure comprising two of the saddle elements described above. These stacked saddle elements are arranged with the second edge surfaces thereof disposed in mated, contacting relationship. This also means that the second ends of the respective crossbars of the two elements are adjacent each other so as to present a generally double x-shaped configuration.

Preferably, the stacked static mixer structure includes four of the saddle elements. The saddle elements are arranged in a first group with the second edge surfaces of the ring-shaped support structures of two of the elements disposed in mated, contacting relationship, and in a second group with the second edge surfaces of the ring-shaped support structures of the other two elements also disposed in mated, contacting relationship. The two groups are stacked so that a first edge surface of a ring-shaped support structure of one group is disposed in mated, contacting relationship with a first edge surface of a ring-shaped support structure of the second group. The net result of this stacking is the provision of two stacked double x-shaped configurations. The four thusly stacked saddle elements provide the particularly preferred arrangement of the invention.

DETAILED DESCRIPTION OF THE PREFERRED EMBODIMENTS

Figure 1:
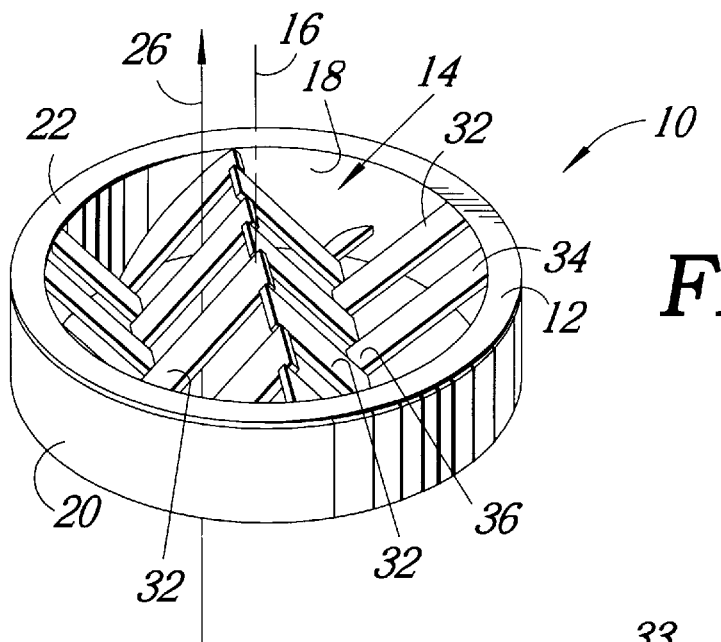
FIG. 1 is an isometric view of a saddle element which embodies the concepts and principles of the invention.
Figure 2:
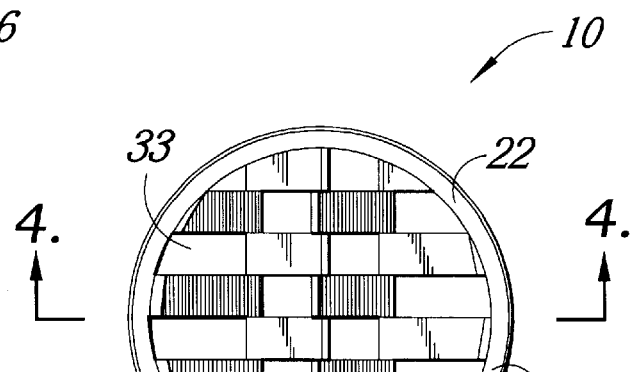
FIG. 2 is a top plan view of the element of FIG. 1.

A preferred embodiment of saddle element for a static mixer which embodies the principles and concepts of the invention is illustrated in FIGS. 1 through 4 of the drawings where it is identified by the reference numeral 10. Saddle element 10 includes a generally ring-shaped support structure 12 and an SMX mixing structure which is broadly identified by the reference numeral 14. In accordance with the invention, the entire element may be cast as a single monolithic unit or the mixing structure 14 and the support structure 12 may be cast as separate units which are then attached by welding or brazing or the like so as to form a single structure.

Figure 4:
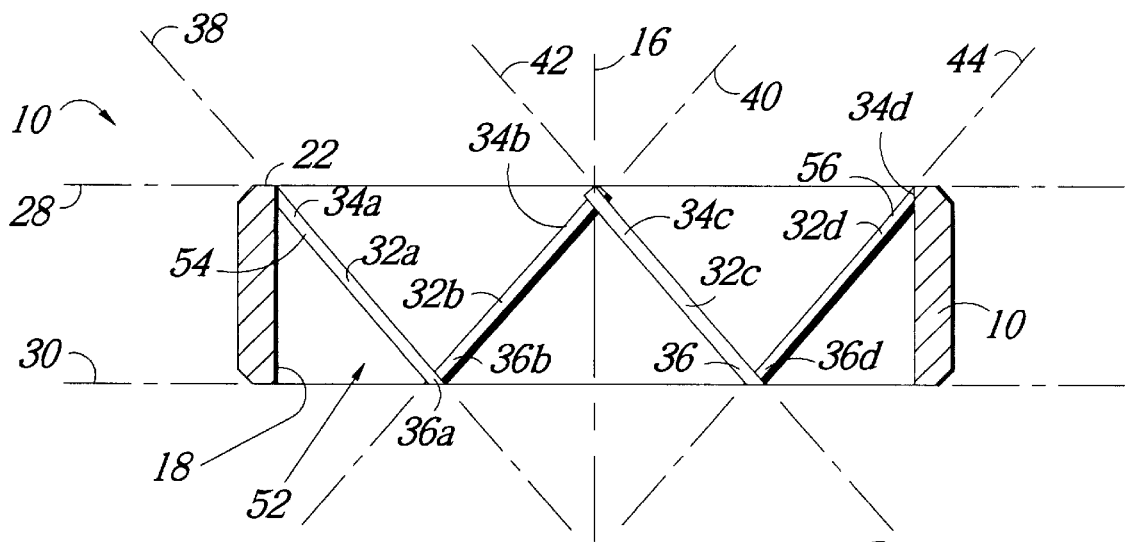
FIG. 4 is an enlarged cross-sectional view of the element of the invention taken along line 4—4 of FIG. 2.

Ring-shaped support structure 12 has a central axis 16, an inner surface 18, an outer surface 20, a first edge surface 22 and a second edge surface 24. Surfaces 18 and 20 are concentrically arranged, preferably generally parallel, and spaced apart radially relative to axis 16, and the same extend circumferentially about structure 12. And as can be seen from the drawings, inner surface 18 defines a fluid flow path shown generally by the arrow 26 and which extends along axis 16. Edge surfaces 22 and 24 are generally planar, and the same are located in respective generally parallel transverse planes 28 and 30 (see FIG. 4) which are spaced apart in an axial direction. As can be seen in FIG. 4, planes 28 and 30 are essentially perpendicular relative to axis 16.

As can best be seen in FIG. 1, mixing structure 14 is made up of a plurality of components in the form of elongated crossbars 32 which are located in flow path 26. In general, each crossbar 32 preferably has a first end 34 which is closer to plane 28 than it is to plane 30, and a second end 36 which is closer to plane 30 than it is to plane 28. Although the crossbars 32 are illustrated as having a generally rectangular configuration, it is within the contemplation of the invention that the same may have other forms, such as, for example round, triangular, oval, square, flat sheet, etc. Moreover, the spaces or passageways between the crossbars may simply be holes in the structure or have any shape other than rectangular.

Figure 3:
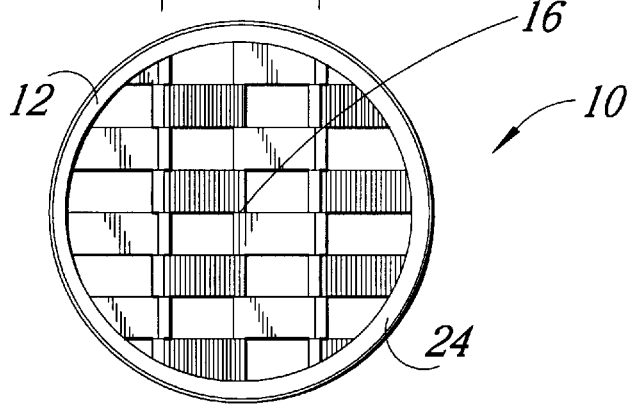
FIG. 3 is a bottom plan view of the element of FIG. 1.

Crossbars 32 may preferably be arranged in at least two, ideally four, separate intersecting oblique planes 38, 40, 42 and 44 which are each disposed at an angle relative to axis 16. Preferably, but not necessarily, the oblique planes intersect at an angle of about 90° relative to one another. The oblique planes are also preferably arranged so that the same are disposed at an angle of about 45° relative to axis 16. However, in accordance with the invention, the crossbar planes may have any other inclination (e.g. 30°, 60°). As can be seen particularly in FIG. 4, planes 38 and 42 are disposed in generally parallel, laterally spaced relationship relative to one another. Likewise, planes 40 and 44 are disposed in generally parallel, laterally spaced relationship relative to one another. Planes 38 and 42 are disposed so as to intersect with planes 40 and 44 along lines 46, 48 and 50 which, as can be seen in FIG. 3, are generally perpendicular to axis 16.

Preferably there are at least two of the crossbars 32 in each plane. The crossbars 32 in each plane are preferably disposed in a generally parallel, laterally spaced relationship relative to one another so as to present spaces or passageways 33 therebetween. And as can be seen in the drawings, the crossbars 32 of one plane are preferably staggered relative to the crossbars of an intersecting plane. That is to say, the crossbars 32 of a given plane are generally disposed in an aligned relationship relative to the spaces 33 of an intersecting plane and in an offset relationship relative to the crossbars 32 of the intersecting plane. Preferably, the arrangement is such that the adjacent crossbars of the intersecting planes are firmly attached to one another along the line of intersection so that a rigid structure is provided. Ideally, there should be at least four crossbars in each plane to achieve optimum mixing capabilities.

With reference to FIG. 4, it can be seen that in a specific arrangement, resulting in the known SMX structure, the respective centrally located crossbars 32*a*, 32*b*, 32*c* and 32*d* of planes 38, 40, 42 and 44 are arranged in an elongated, generally w-shaped array 52 which extends laterally across flow path 26. As can be seen, the ends 54 and 56 of array 52 are each attached to inner surface 18 at a location which is adjacent to surface 22. With further reference to FIG. 4, it can also be seen that planes 40 and 42 intersect at line 48 (also see FIG. 3) which is disposed at or near plane 28. Line 48 is preferably positioned centrally of flow path 26 so as to essentially intersect with axis 16.

The ends 34 of the crossbars of planes 40 and 42 intersect and/or are attached together at line 48. The form of intersection at line 48 can be made such that the crossbars simply overlap, or the intersection may be flat or round or present a sharp edge. It is also possible to reinforce the structure at line 48 or to facilitate casting by adding additional thickness and material in this region to the crossbars. The same applies to the intersection line 46 of planes 38 and 40 and the intersection line 50 of planes 42 and 44, near the opposite plane 30.

Ideally, as can be seen in FIG. 4, the arrangement is such that end 34a of crossbar 32a of plane 38 is firmly attached to inner surface 18 of the ring-shaped support structure 12 at a point near plane 28, end 36a of crossbar 32a is firmly attached to end 36b of crossbar 32b of plane 40 at a point near plane 30, and end 34b of crossbar 32b is firmly attached to end 34c of crossbar 32c of plane 42 at a point near plane 28 and near line 48 which extends through axis 16. Similarly, end 34d of crossbar 32d of plane 44 is firmly attached to inner surface 18 of the ring-shaped support structure 12 at a point near plane 28, and end 36d of crossbar 32d is firmly attached to end 36c of crossbar 32c of plane 42 at a point near plane 30. Additional material and a radius might be added at all crossing or attachment lines for reinforcement and/or to facilitate casting.

Figure 5:
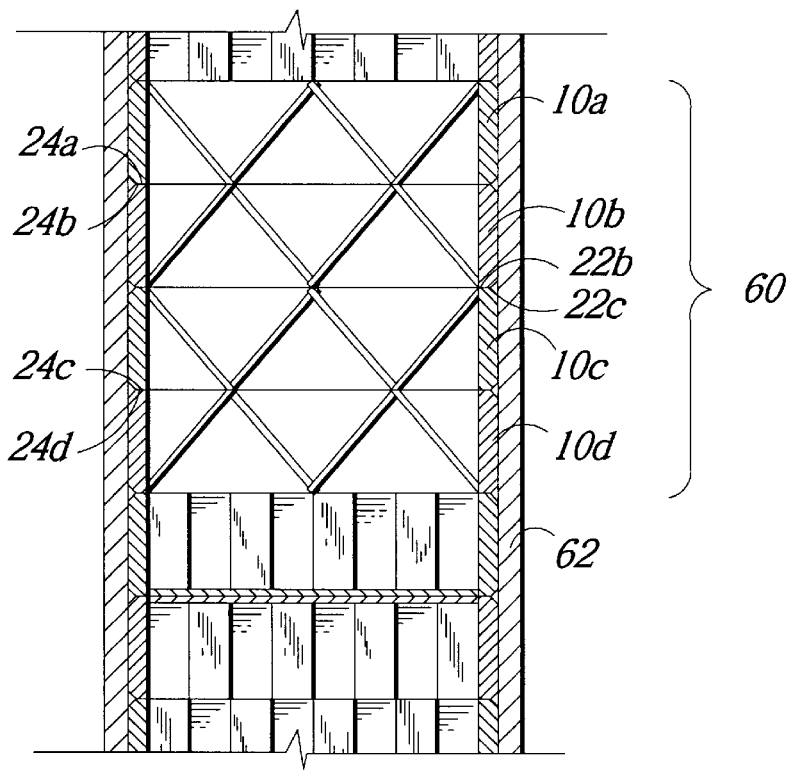
FIG. 5 is an elevational cross-sectional view of a stack comprising a plurality of the elements of FIG. 1.

The saddle elements 10 of the invention are generally and preferably used in structures which include a plurality of the same. Such an arrangement is illustrated in FIG. 5 of the drawings. In a preferred arrangement illustrated in FIG. 5, an element 10a and an element 10b, each of which are the same as the element 10 described above, are arranged such that the surfaces 24a and 24b thereof are disposed in mated, contacting relationship. Similarly, an element 10c and an element 10d, each of which are also the same as the element 10 described above, are arranged such that the surfaces 24c and 24d thereof are disposed in mated, contacting relationship. In addition, the surface 22b of element 10b and the surface 22c of element 10c are disposed in mated, contacting relationship. This arrangement provides a static mixer structure 60 which is made up of four sequentially flip-flopped individual elements 10. The structure 60 may then preferably be placed in a pipe 62 for added support. As will be appreciated by those of ordinary skill in the art, for a given installation, a plurality of structures 60 may be employed. In this event, it may be preferable to rotate adjacent structures 60 relative to one another as shown in FIG. 5. Ideally, axially adjacent structures 60 may be rotated about 90° relative to one another. While the structures 60 preferably include adjacent, contacting elements 10, it should be appreciated that spacer rings could be provided between the elements 10 to facilitate a particular application.

Figure 6A:
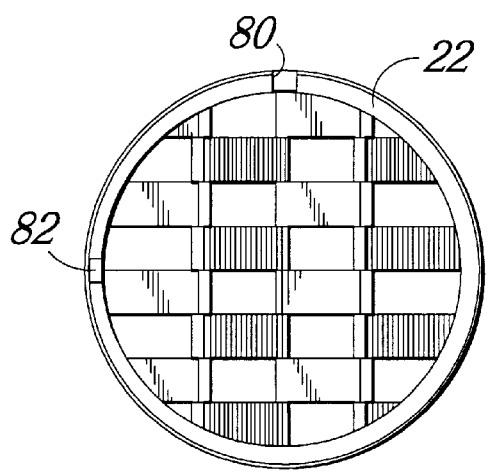
FIGS. 6A, 6B and 6C are respectively top plan, bottom plan and cross-sectional views illustrating an embodiment of the invention wherein the support structure 12 is provided with alignment tabs and notches.
Figure 6B:
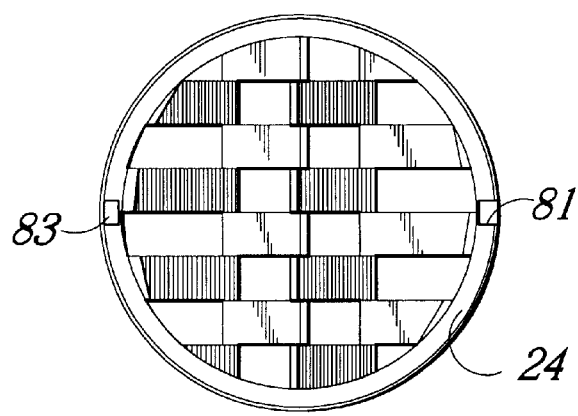
Figure 6C:
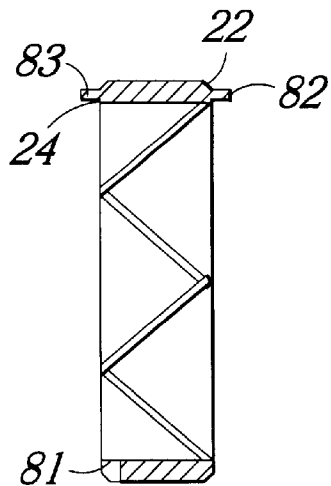

The structure 60 is only a possible arrangement of saddles elements 10 according to this invention. Other possible arrangements would include, for example, (1) having all of the stacked saddle elements 10 arranged in the same orientation, (2) having each of the stacked elements 10 always rotated relative to adjacent elements 10, and (3) having the stacked elements 10 arranged randomly and/or aperiodic. In one preferred arrangement which facilitates the arrangement of the stacked saddle elements 10, the same are equipped with notches and tabs or other registration means at the edge surfaces 22 and 24 of the support ring 12 as shown in FIGS. 6A, 6B and 6C. In this case a tab 82 is located on edge surface 22 of ring 12 and another tab 83 is located on edge surface 24 of ring 12. Tabs 82 and 83 are disposed in longitudinal alignment relative to ring 12 at positions which are offset circumferentially essentially 90° relative to intersecting line 48. A notch 81 having a mating shape relative to tabs 82 and 83 is located at edge surface 22 of support ring 12 at a position directly opposite tab 82. Another notch 80 which also has a mating shape relative to tabs 82 and 83 is located at edge surface 24 of ring 12 at a position which is offset 90° from tab 82. This special arrangement of notches 80, 81 and tabs 82, 83 forces the user or an automated assembling machine to assemble the stack in such a way that two saddle elements 10 having the same orientation are stacked in a first group, followed by another group of two saddle elements 10 where the orientation is 90° rotated. This results in a static mixer structure similar to a SMX mixing element having mixing elements of L/D=0.5.

A standard static mixer element 10 which embodies the principles and concepts of the invention is typically made of about 2–16 intersecting crossbars 32 which are inclined at an angle of approximately 45° relative to axis 16. The axial length of each element is typically about 0.25 times the pipe diameter. Thus, a structure 60 which includes four elements 10 will have an axial length which is approximately equal to the diameter of the pipe. The support ring 12 preferentially has the same axial length as the height of the w-shape structure 52, but it might also be longer at one or both ends in order to leave empty spaces when the saddles are stacked in a structure.

In accordance with the invention, a static mixer is provided which comprises a stack of individual ring-shaped support structures 12, each of which ring-shaped support structures 12 supports a saddle 14 of SMX structure, as shown in the drawings. The individual elements can be produced using inexpensive precision casting in a simple mold. A stack of such pieces may be disassembled for cleaning and visual inspection. Because the ring-shaped support structure and the SMX saddle may be formed as a single integral piece, no expensive, machined pieces are needed. The strength is increased at least four-fold in comparison to conventional construction. This allows for the use of thinner materials with resulting reduction in pressure drop. Use of these elements in polymer mixers facilitates the employment of standard pipes that can be fully inspected. The elements can be removed and cleaned. The simple construction of elements of the invention enables the manufacture of the same out of plastic using conventional injection molding. The plastic static mixer elements may be used in applications where disposable parts are desirable.

The features of the present invention facilitate:
1) the use of an arrangement whereby four saddles having the same orientation are stacked in a first group, followed by another four saddle group where the orientation is rotated 90°;
2) the use of an arrangement whereby two saddles having the same orientation are stacked in a first group, followed by another two saddle group where the orientation is rotated 90°;
3) the casting or injection molding of each saddle as a single structure with a surrounding ring-shaped support structure;
4) the orientation of the individual elements by providing notches and tabs or other registration means in the ring-shaped support structures and/or saddles, whereby the structures may be regularly or chaotically oriented at will;
5) the use of ring-shaped support structures or saddles which are not the same in structure, particularly to provide, for example, alternating patterns of crossbars and passages and/or different inclinations or shapes of crossbars;
6) the use of saddles which are made up of individual cast or welded bars, or which are made by crimping of perforated plates, with or without a ring-shaped support structure;
7) the use of ring-shaped support structures which are welded, brazed or glued to a rod of mixer components.

I claim:

1. A saddle element for a static mixer comprising:
    a generally ring-shaped support structure having a central axis, concentric inner and outer, radially spaced, circumferentially extending surfaces, and first and second axially spaced, generally parallel edge surfaces, said inner surface defining a fluid flow path which extends along said axis,
    said edge surfaces being located in respective generally parallel transverse planes which are essentially perpendicular relative to said axis; and
    a plurality of mixer components located in said flow path, said components having a first end which is closer to the transverse plane of said first edge than to the transverse plane of the second edge and a second end which is closer to the transverse plane of said second edge than to the transverse plane of the first edge,
    said mixer components being arranged in at least two separate intersecting oblique planes, each of which intersecting oblique planes is disposed at an angle relative to said axis, there being a plurality of said components in each said plane, which components of each plane are spaced apart to provide openings for fluid flow.

2. A saddle element as set forth in claim 1, wherein said components comprise crossbars, and wherein the respective crossbars of each plane are disposed in a generally parallel relationship relative to one another.

3. A saddle element as set forth in claim 1, wherein said components are arranged in four separate oblique planes, said oblique planes being arranged in two separate pairs of oblique planes, the oblique planes of each pair being disposed in generally parallel, laterally spaced relationship relative to one another, the oblique planes of each pair being disposed so as to intersect the oblique planes of the other pair along lines which are generally perpendicular to said axis.

4. A saddle element as set forth in claim 3, wherein said components are crossbars and at least two of said crossbars are arranged in each of said intersecting oblique planes, and wherein the crossbars of each oblique plane are disposed in generally parallel, laterally spaced relationship.

5. A saddle element as set forth in claim 4, wherein about 4 to 8 crossbars are arranged in each of said oblique planes.

6. A saddle element as set forth in claim 1, wherein said element comprises registration means for aligning the element with an adjacent element in a stack of elements.

7. A saddle element as set forth in claim 6, wherein said registration means comprises mating tab and notch elements.

8. A saddle element as set forth in claim 6, wherein said registration means comprises a first tab located on the first edge surface, a second tab located on the second edge surface, a first notch having a mating shape relative to said tabs located at said first edge surface and a second notch which also has a mating shape relative to said tabs located at said second edge surface, said tabs and said notches being positioned so as to cause the element to adopt a preestablished position relative to an adjacent saddle element.

9. A saddle element as set forth in claim 8, wherein said tabs are disposed in longitudinal alignment relative to the support structure at positions which are offset circumferentially essentially 90° relative to a plane which includes said axis and is parallel to a line where said oblique planes intersect.

10. A saddle element as set forth in claim 9, wherein said notches are offset 90° about said support structure relative to one another.

11. A saddle element as set forth in claim 10, wherein the notch at the first edge surface is positioned directly opposite the tab on said first edge surface.

12. A saddle element as set forth in claim 8, wherein said notches are offset 90° about said support structure relative to one another.

13. A saddle element for a static mixer comprising:
    a generally ring-shaped support structure having a central axis, concentric inner and outer, radially spaced, circumferentially extending surfaces, and first and second axially spaced, generally parallel edge surfaces, said inner surface defining a fluid flow path which extends along said axis,
    said edge surfaces being located in respective generally parallel transverse planes which are essentially perpendicular relative to said axis; and
    a plurality of mixer components located in said flow path, said components having a first end which is closer to the transverse plane of said first edge than to the transverse plane of the second edge and a second end which is closer to the transverse plane of said second edge than to the transverse plane of the first edge,
    said mixer components being arranged in at least four separate oblique planes, each of which oblique planes is disposed at an angle relative to said axis, said oblique planes being arranged in two separate pairs of oblique planes, the oblique planes of each pair being disposed in generally parallel, laterally spaced relationship relative to one another, the oblique planes of each pair being disposed so as to intersect the oblique planes of the other pair along lines which are generally perpendicular to said axis,
    wherein said components comprise crossbars arranged in an elongated, generally w-shaped array having a pair of spaced ends, said array being disposed to extend laterally across said flow path with each end thereof being attached to said inner surface.

14. A saddle element as set forth in claim 13, wherein at least two of said crossbars are arranged in each of said intersecting oblique planes, and wherein the crossbars of each oblique plane are disposed in generally parallel, laterally spaced relationship.

15. A saddle element as set forth in claim 14, wherein two of said oblique planes intersect at a line disposed essentially in the transverse plane of said first edge and which extends through said axis, the first ends of the crossbars of said two of said oblique planes being connected together near said line.

16. A saddle element as set forth in claim 15, wherein the first end of a selected crossbar of a first oblique plane is attached to said inner surface at a location adjacent said first edge, the second end of a selected crossbar of a second oblique plane is attached to the second end of the selected crossbar of the first oblique plane, the first end of said selected crossbar of said second oblique plane is connected to the first end of a selected crossbar of a third oblique plane, the second end of said selected crossbar of said third oblique plane is attached to the second end of a selected crossbar of a fourth oblique plane, and the first end of the selected crossbar of the fourth oblique plane is attached to said inner surface at a location adjacent said first edge, said selected crossbars extending laterally across said fluid flow path and presenting said w-shaped array.

17. A static mixer structure comprising two of the saddle elements of claim 16, said saddle elements being arranged with the second edge surfaces thereof disposed in mated, contacting relationship.

18. A static mixer structure comprising a first, a second, a third and a fourth of the saddle elements of claim 16, said saddle elements being arranged with the second edge surfaces of said first and second elements disposed in mated, contacting relationship, with the second edge surfaces of said third and fourth elements disposed in mated, contacting relationship, and with the first edge surfaces of said second and third elements disposed in mated, contacting relationship.

19. A saddle element as set forth in claim 15, wherein said intersecting oblique planes intersect at an angle of about 90°.

20. A saddle element as set forth in claim 15, wherein said oblique planes are disposed at an angle of about 45° relative to said axis.

21. A static mixer structure comprising two saddle elements, each said saddle element comprising:

a generally ring-shaped support structure having a central axis, concentric inner and outer, radially spaced, circumferentially extending surfaces, and first and second axially spaced, generally parallel edge surfaces, said inner surface defining a fluid flow path which extends along said axis, said edge surfaces being located in respective generally parallel transverse planes which are essentially perpendicular relative to said axis; and a plurality of mixer components located in said flow path, said components having a first end which is closer to the transverse plane of said first edge than to the transverse plane of the second edge and a second end which is closer to the transverse plane of said second edge than to the transverse plane of the first edge, said mixer components being arranged in at least two separate intersecting oblique planes, each of which intersecting oblique planes is disposed at an angle relative to said axis, there being a plurality of said components in each said plane, which components of each plane are spaced apart to provide openings for fluid flow, said saddle elements being arranged with the second edge surfaces thereof disposed in mated, contacting relationship.

22. A static mixer structure comprising first, second, third and fourth saddle elements, each said saddle element comprising:

a generally ring-shaped support structure having a central axis, concentric inner and outer, radially spaced, circumferentially extending surfaces, and first and second axially spaced, generally parallel edge surfaces, said inner surface defining a fluid flow path which extends along said axis, said edge surfaces being located in respective generally parallel transverse planes which are essentially perpendicular relative to said axis; and a plurality of mixer components located in said flow path, said components having a first end which is closer to the transverse plane of said first edge than to the transverse plane of the second edge and a second end which is closer to the transverse plane of said second edge than to the transverse plane of the first edge, said mixer components being arranged in at least two separate intersecting oblique planes, each of which intersecting oblique planes is disposed at an angle relative to said axis, there being a plurality of said components in each said plane, which components of each plane are spaced apart to provide openings for fluid flow, said saddle elements being arranged with the second edge surfaces of said first and second elements disposed in mated, contacting relationship, with the second edge surfaces of said third and fourth elements disposed in mated, contacting relationship, and with the first edge surfaces of said second and third elements disposed in mated, contacting relationship.

* * * * *

(12) EX PARTE REEXAMINATION CERTIFICATE (6401st)
United States Patent
Streiff

(10) Number: US 6,394,644 C1
(45) Certificate Issued: Aug. 26, 2008

(54) STACKED STATIC MIXING ELEMENTS

(75) Inventor: Felix A. Streiff, Humlikon (CH)

(73) Assignee: Sulzer Chemtech AG, Winterthur (CH)

Reexamination Request:
No. 90/007,199, Sep. 10, 2004

Reexamination Certificate for:
Patent No.: 6,394,644
Issued: May 28, 2002
Appl. No.: 09/596,499
Filed: Jun. 19, 2000

Related U.S. Application Data

(60) Provisional application No. 60/140,336, filed on Jun. 21, 1999.

(51) Int. Cl.
*B01F 5/06* (2006.01)

(52) U.S. Cl. .................................................. 366/337
(58) Field of Classification Search ............... 366/181.5, 366/336, 337, 340; 261/112.1; 138/37–40, 138/42; 48/189.4; 222/145.6, 459
See application file for complete search history.

(56) References Cited

U.S. PATENT DOCUMENTS 1,857,348 A * 5/1932 Bokenkroger ................ 55/446
5,564,827 A * 10/1996 Signer ......................... 366/336
6,109,781 A * 8/2000 Ogasawara et al. ......... 366/336

FOREIGN PATENT DOCUMENTS

CZ      1707 U   *   6/1994

* cited by examiner

Primary Examiner—David L Sorkin

(57) ABSTRACT

A saddle element for a static mixer includes a generally ring-shaped support structure having a central axis, concentric inner and outer, radially spaced, circumferentially extending surfaces, and first and second axially spaced, generally parallel edge surfaces. The inner surface of the ring-shaped support structure defines a fluid flow path which extends along the central axis. The edge surfaces of the ring-shaped support structure are located in respective generally parallel transverse planes which are essentially perpendicular relative to the central axis. The saddle element also includes a plurality of crossbars that are located in the flow path. The crossbars have a first end which is closer to the transverse plane of the first edge of the ring-shaped support structure than to the transverse plane of the second edge of the ring-shaped support structure. The crossbars also have a second end which is closer to the transverse plane of the second edge of the ring-shaped support structure than to the transverse plane of the first edge of the ring-shaped support structure. The crossbars are arranged in at least two separate intersecting oblique planes, each of which intersecting oblique planes is disposed at an angle relative to the central axis. The saddle elements may be used in a structure which includes four flip-flopped stacked elements.

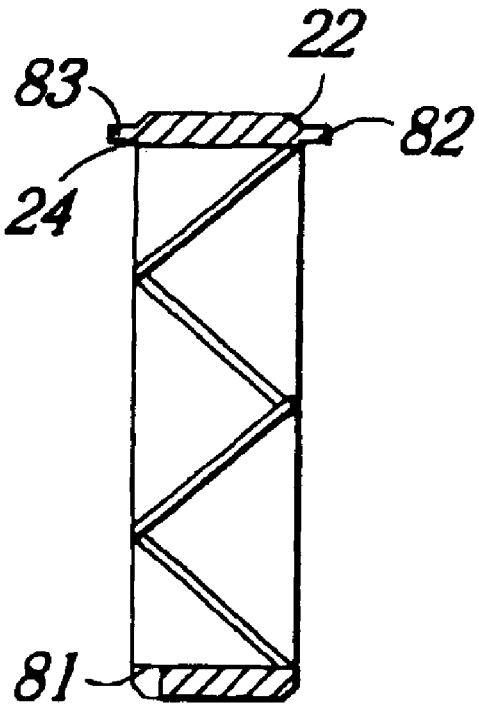

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–7 and 13–22 are cancelled.

Claim 8 is determined to be patentable as amended.

Claims 9–12, dependent on an amended claim, are determined to be patentable.

New claims 23–25 are added and determined to be patentable.

8. A saddle element [as set forth in claim 6, wherein] *for a static mixer* comprising:
- a generally ring-shaped support structure having a central axis, concentric inner and outer, radially spaced, circumferentially extending surfaces, and first and second axially spaced, generally parallel edge surfaces, said inner surface defining a fluid flow path which extends along said axis,
- said edge surfaces being located in respective generally parallel transverse planes which are essentially perpendicular relative to said axis;
- a plurality of mixer components located in said flow path, said components having a first end which is closer to the transverse plane of the said first edge than to the transverse plane of the second edge and a second end which is closer to the transverse plane of said second edge than to the transverse plane of the first edge,
- said mixer components being arranged in at least two separate intersecting oblique planes, each of which intersecting oblique planes is disposed at an angle relative to said axis, there being a plurality of said components in each said plane, which components of each plane are spaced apart to provide openings for fluid flow; and
- registration means for aligning the elements with an adjacent element in a stack of elements, said registration means [comprises] *comprising* a first tab located on the first edge surface, a second tab located on the second edge surface, a first notch having a mating shape relative to said tabs located at said first edge surface and a second notch which also has a mating shape relative to said tabs located at said second edge surface, said tabs and said notches being positioned so as to cause the element to adopt a preestablished position relative to an adjacent saddle element.

*23. A static mixer structure comprising*
- *a stack of saddle elements separately mounted on a common axis to permit individual removal of said saddle elements from each other,*
- *each said saddle element comprising*
- *a generally ring-shaped support structure having a central axis, concentric inner and outer radially spaced circumferentially extending surfaces, and first and second axially spaced generally parallel edge surfaces, said inner surface defining a fluid flow path extending along said axis, said edge surfaces being located in respective generally parallel transverse planes essentially perpendicular relative to said axis; and*
- *a mixing structure located in said flow path between said edge surfaces and including a plurality of mixer components, each of said mixer components having a first end located between said edge surfaces and closer to said transverse plane of said first edge than to said transverse plane of said second edge and a second end located between said edge surfaces and closer to said transverse plane of said second edge than to said transverse plane of said first edge,*
- *said mixer components being arranged in at least two separate intersecting oblique planes, each of said oblique planes being disposed at an angle relative to said axis, there being a plurality of said components in each said plane, which components of each plane are spaced apart to provide openings for fluid flow, said mixer components comprising crossbars with at least two of said crossbars arranged in each of said intersecting oblique planes in laterally spaced relationship.*

*24. A static mixer structure as set forth in claim 23 further characterized in having said stack of said saddle elements disposed in a pipe.*

*25. A static mixer structure as set forth in claim 23 further characterized in each said saddle element having a registration means for aligning said element with an adjacent element in said stack of elements.*

\* \* \* \* \*

(12) INTER PARTES REEXAMINATION CERTIFICATE (618th)
United States Patent
Streiff

(10) Number: US 6,394,644 C2
(45) Certificate Issued: Jun. 10, 2013

(54) STACKED STATIC MIXING ELEMENTS

(75) Inventor: Felix A. Streiff, Humlikon (CH)

(73) Assignee: Sulzer Chemtech AG, Winterthur (CH)

Reexamination Request:
No. 95/000,525, Dec. 22, 2009

Reexamination Certificate for:
Patent No.: 6,394,644
Issued: May 28, 2002
Appl. No.: 09/596,499
Filed: Jun. 19, 2000

Reexamination Certificate C1 6,394,644 issued Aug. 26, 2008

Related U.S. Application Data

(60) Provisional application No. 60/140,336, filed on Jun. 21, 1999.

(51) Int. Cl.
*B01F 5/06* (2006.01)

(52) U.S. Cl.
USPC ................................................ 366/337

(58) Field of Classification Search
None
See application file for complete search history.

(56) References Cited

To view the complete listing of prior art documents cited during the proceeding for Reexamination Control Number 95/000,525, please refer to the USPTO's public Patent Application Information Retrieval (PAIR) system under the Display References tab.

*Primary Examiner* — Krisanne Jastrzab

(57) ABSTRACT

A saddle element for a static mixer includes a generally ring-shaped support structure having a central axis, concentric inner and outer, radially spaced, circumferentially extending surfaces, and first and second axially spaced, generally parallel edge surfaces. The inner surface of the ring-shaped support structure defines a fluid flow path which extends along the central axis. The edge surfaces of the ring-shaped support structure are located in respective generally parallel transverse planes which are essentially perpendicular relative to the central axis. The saddle element also includes a plurality of crossbars that are located in the flow path. The crossbars have a first end which is closer to the transverse plane of the first edge of the ring-shaped support structure than to the transverse plane of the second edge of the ring-shaped support structure. The crossbars also have a second end which is closer to the transverse plane of the second edge of the ring-shaped support structure than to the transverse plane of the first edge of the ring-shaped support structure. The crossbars are arranged in at least two separate intersecting oblique planes, each of which intersecting oblique planes is disposed at an angle relative to the central axis. The saddle elements may be used in a structure which includes four flip-flopped stacked elements.

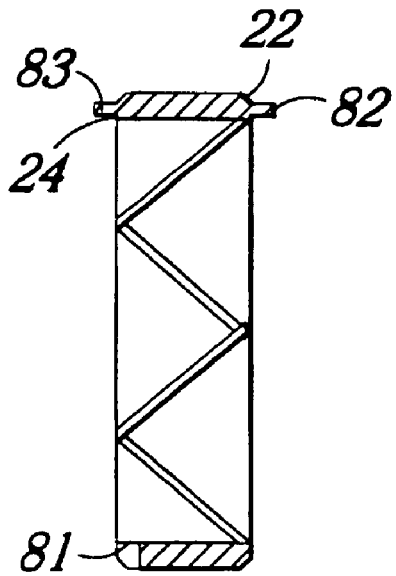

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-7 and 13-22 were previously cancelled.
Claims 8-12 and 23-25 are cancelled.

\* \* \* \* \*